(12) United States Patent
Parker et al.

(10) Patent No.: US 8,790,435 B2
(45) Date of Patent: Jul. 29, 2014

(54) METHOD TO IMPROVE MUSHROOM CULTIVATION

(76) Inventors: Frank Henry Parker, Nr Buxton (GB); Stuart Glaister Whitehall, Macclesfield (GB)

( * ) Notice: Subject to any disclaimer, the term of this patent is extended or adjusted under 35 U.S.C. 154(b) by 0 days.

(21) Appl. No.: 12/991,677

(22) PCT Filed: Mar. 16, 2009

(86) PCT No.: PCT/GB2009/000705
§ 371 (c)(1),
(2), (4) Date: Nov. 8, 2010

(87) PCT Pub. No.: WO2009/136132
PCT Pub. Date: Nov. 12, 2009

(65) Prior Publication Data
US 2011/0094276 A1 Apr. 28, 2011

(30) Foreign Application Priority Data
May 7, 2008 (GB) .................................. 0808230.7

(51) Int. Cl.
| | | |
|---|---|---|
| *A01G 1/04* | (2006.01) | |
| *A01H 15/00* | (2006.01) | |
| *A01H 17/00* | (2006.01) | |
| *A01N 57/00* | (2006.01) | |
| *A01N 59/00* | (2006.01) | |
| *A01N 65/00* | (2009.01) | |
| *C05D 1/00* | (2006.01) | |
| *C05D 3/00* | (2006.01) | |
| *C05D 5/00* | (2006.01) | |

(52) U.S. Cl.
CPC *A01G 1/04* (2013.01); *A01G 1/044* (2013.01); *A01G 1/042* (2013.01); *A01G 1/046* (2013.01); *A01G 1/048* (2013.01); *A01H 15/00* (2013.01); *A01H 17/00* (2013.01); *A01N 57/00* (2013.01); *A01N 59/00* (2013.01); *A01N 65/00* (2013.01); *C05D 1/00* (2013.01); *C05D 3/00* (2013.01); *C05D 5/00* (2013.01)
USPC .................................................... 71/5; 47/1.1

(58) Field of Classification Search
CPC ......... A01G 1/04; A01G 1/044; A01G 1/042; A01G 1/046; A01G 1/048; A01H 15/00; A01H 17/00; A01N 57/00; A01N 59/00; A01N 65/00; C05D 1/00; C05D 3/00; C05D 5/00
USPC ................................................. 71/5–9; 47/1.1
See application file for complete search history.

(56) References Cited

U.S. PATENT DOCUMENTS 5,186,731 A 2/1993 Parker
(Continued)

FOREIGN PATENT DOCUMENTS

EP 0 407 142 A 1/1991
(Continued)

OTHER PUBLICATIONS

WIPO Publication WO1993013647 A1, Jul. 22, 1993 to Dahlberg et al., p. 1, lines 8-15.
(Continued)

*Primary Examiner* — Jennifer A Smith
(74) *Attorney, Agent, or Firm* — Jackson Patent Law Office

(57) ABSTRACT

A method to improve the function and performance of the mushroom bed which comprises nutritionally supplementing the mushroom bed by mixing very small amounts of carboxylic acid salts into the casing layer or on the surface of the compost in close proximity to the casing layer of chalk and peat soils as commercially utilized. The salt may be derived from an aliphatic, alicyclic, heterocyclic or aromatic carboxylic acid and mixtures thereof. The cations may include potassium magnesium and preferably calcium and mixtures thereof for both casing additions and compost surface application. For compost surface additions only, ammonia and organic amines may also be used as cations. The carboxylic salts may be mixed with other nutrient substances to further improve performance.

17 Claims, 10 Drawing Sheets

(56) References Cited

U.S. PATENT DOCUMENTS

| | | | |
|---|---|---|---|
| 5,681,738 A | * | 10/1997 | Beelman et al. ........... 435/254.1 |
| 5,888,803 A | * | 3/1999 | Starkey .................... 435/254.1 |
| 2008/0148629 A9 | * | 6/2008 | Stamp ............................. 47/1.1 |

FOREIGN PATENT DOCUMENTS

| | | |
|---|---|---|
| FR | 2 550 913 A | 3/1985 |
| GB | 2 146 319 A | 4/1985 |
| WO | WO 95/34521 A | 12/1995 |

OTHER PUBLICATIONS

European Patent EP0038457 B1, Dec. 27, 1984 to Hanacek et al., p. 1, line 38 to p. 2, line 5.

European Patent EP0407142 B1, Aug. 31, 1994 to Parker, p. 2, lines 30-32.

The Cultivation of Mushrooms, Ed. Professor L. J. L. D van Griensven. Published 1988, Horst Chapter 3. pp. 73-75 H.R. Visscher.

* cited by examiner

Case run compost. Temperature over control. Degrees Centigrade

| | am Day 1 | pm Day 1 | am Day 2 | pm Day 2 | am Day 3 | pm Day 3 | am Day 4 | pm Day 4 | am Day 5 | pm Day 5 | am Day 6 | pm Day 6 | am Day 7 | pm Day 7 |
|---|---|---|---|---|---|---|---|---|---|---|---|---|---|---|
| Test Bed 1 Control | 23 | 23.5 | 24 | 24 | 25 | 25.5 | 25 | 25 | 24.5 | 25 | 24.5 | 24 | 24.5 | 24.5 |
| | am Day 1 | pm Day 1 | am Day 2 | pm Day 2 | am Day 3 | pm Day 3 | am Day 4 | pm Day 4 | am Day 5 | pm Day 5 | am Day 6 | pm Day 6 | am Day 7 | pm Day 7 |
| Test Bed 2 | 0 | 0.5 | 1 | 1.5 | 1 | 1 | 1 | 0.5 | 0.5 | 0 | 0.5 | 0.5 | 0.5 | 0 |
| Test Bed 3 | 0.5 | 0.5 | 1.5 | 1 | 1 | 1 | 1 | 0.5 | 0.5 | 0 | 0.5 | 0 | 0.5 | 0.5 |
| Test Bed 4 | 0 | 0.5 | 1 | 1.5 | 1 | 0.5 | 1 | 0.5 | 0.5 | 0.5 | 0 | 0.5 | 0.5 | 0 |
| Test Bed 5 | 0 | 0.5 | 1 | 1 | 1.5 | 1 | 0.5 | 0.5 | 0.5 | 0.5 | 0.5 | 0.5 | 0.5 | 0.5 |
| Test Bed 6 | 0.5 | 0.5 | 1 | 1.5 | 2 | 2 | 1 | 1 | 1 | 0.5 | 0.5 | 0.5 | 0 | 0 |
| Test Bed 7 | 0.5 | 1 | 1 | 1.5 | 2 | 2 | 1 | 1 | 0.5 | 0.5 | 0 | 0.5 | 0.5 | 0.5 |
| Test Bed 8 | 0.5 | 0.5 | 1 | 1 | 1.5 | 1.5 | 1.5 | 1 | 0.5 | 0 | 0.5 | 0.5 | 0 | 0 |
| Test Bed 9 | 0.5 | 0.5 | 1 | 1 | 1 | 1.5 | 1.5 | 1 | 0.5 | 0.5 | 0.5 | 0 | 0 | 0.5 |
| Test Bed 10 | 0 | 0.5 | 0.5 | 0.5 | 1.5 | 1 | 1.5 | 1 | 1 | 0.5 | 0.5 | 0.5 | 0 | 0.5 |
| Test Bed 11 | 0.5 | 0.5 | 0.5 | 1 | 1 | 1.5 | 1 | 1 | 0.5 | 0.5 | 0 | 0 | 0 | 0 |
| Test Bed 12 | 0 | 0.5 | 0.5 | 0.5 | 1 | 1.5 | 1.5 | 0.5 | 0.5 | 0.5 | 0.5 | 0 | 0.5 | 0.5 |
| Test Bed 13 | 0 | 0.5 | 0.5 | 0.5 | 1 | 1.5 | 1 | 1 | 1 | 0.5 | 0 | 0.5 | 0.5 | 0.5 |
| Test Bed 14 | 0 | 0.5 | 0.5 | 0.5 | 1.5 | 1.5 | 1 | 0.5 | 0.5 | 0.5 | 0.5 | 0 | 0.5 | 0.5 |
| Test Bed 15 | 0.5 | 0.5 | 0.5 | 0.5 | 1.5 | 1.5 | 1 | 0.5 | 0.5 | 0.5 | 0.5 | 0.5 | 0.5 | 0.5 |
| Test Bed 16 | 2.5 | 2.5 | 3 | 3.5 | 4.5 | 5 | 2.5 | 2.5 | 2.5 | 1.5 | 2 | 1.5 | 1.5 | 1 |

Figure 1

Test Bed 1 – Control No additions to casing or compost

| | Flush 1 | Flush 2 | Cumulative | Flush 3 | Cumulative |
|---|---|---|---|---|---|
| Flush Weight Kg | 9600 | 9550 | 19150 | 5550 | 24700 |

Test Bed 2.  55grams Calcium Maleate mixed in 1 square metre casing. No additions to compost

| | Flush 1 | Flush 2 | Cumulative | Flush 3 | Cumulative |
|---|---|---|---|---|---|
| Flush Weight Kg | 9850 | 10850 | 20700 | 5050 | 25750 |

Test Bed 3.  110grams Calcium Maleate mixed in 1 square metre casing. No additions to compost

| | Flush 1 | Flush 2 | Cumulative | Flush 3 | Cumulative |
|---|---|---|---|---|---|
| Flush Weight Kg | 12030 | 12950 | 24980 | 4850 | 29830 |

Test Bed 4.  165grams Calcium Maleate in 1 square metre casing. No additions to compost

| | Flush 1 | Flush 2 | Cumulative | Flush 3 | Cumulative |
|---|---|---|---|---|---|
| Flush Weight Kg | 12015 | 12850 | 24865 | 4895 | 29760 |

Figure 3

Test Bed 5.   220 Calcium Maleate mixed in 1 square metre casing. No additions to compost

| | Flush 1 | Flush 2 | Cumulative | Flush 3 | Cumulative |
|---|---|---|---|---|---|
| Flush Weight Kg | 10675 | 10005 | 20680 | 4705 | 25385 |

Test Bed 6.   165grams Calcium Maleate mixed in compost. No additions to casing.

| | Flush 1 | Flush 2 | Cumulative | Flush 3 | Cumulative |
|---|---|---|---|---|---|
| Comparative Example | | | | | |
| Flush Weight Kg | 9625 | 9600 | 19225 | 5505 | 24730 |

Test Bed 7.   220grams Calcium Maleate mixed in compost. No additions to casing

| | Flush 1 | Flush 2 | Cumulative | Flush 3 | Cumulative |
|---|---|---|---|---|---|
| Comparative example | | | | | |
| Flush Weight Kg | 9590 | 9595 | 19185 | 5700 | 24885 |

Test Bed 8.   55grams Calcium Maleate on casing/compost interface. No additions to compost or casing

| | Flush 1 | Flush 2 | Cumulative | Flush-3 | Cumulative |
|---|---|---|---|---|---|
| Flush Weight Kg | 11050 | 10030 | 21080 | 4850 | 25930 |

Figure 5

Test Bed 9.

110grams Calcium Maleate on casing/compost interface. No additions to compost or casing

| | Flush 1 | Flush 2 | Cumulative | Flush 3 | Cumulative |
|---|---|---|---|---|---|
| Flush Weight Kg | 13005 | 12000 | 25005 | 4950 | 29955 |

Test Bed 10.

165 grams Calcium Maleate on casing/compost interface. No additions to compost or casing

| | Flush 1 | Flush 2 | Cumulative | Flush 3 | Cumulative |
|---|---|---|---|---|---|
| Flush Weight Kg | 13630 | 13050 | 26680 | 5000 | 31680 |

Test Bed 11.

220grams Calcium Maleate on casing/compost interface. No additions to compost or casing

| | Flush 1 | Flush 2 | Cumulative | Flush 3 | Cumulative |
|---|---|---|---|---|---|
| Flush Weight Kg | 10500 | 12050 | 22550 | 4905 | 27455 |

Test Bed 12.

1100ml of 10% aqueous dispersion of Calcium Maleate on casing/compost interface.
No additions to compost or casing

| | Flush 1 | Flush 2 | Cumulative | Flush 3 | Cumulative |
|---|---|---|---|---|---|
| Flush Weight Kg | 13000 | 11905 | 24905 | 4905 | 29810 |

Figure 7

Test Bed 13. 2200ml of 10% aqueous dispersion of Calcium Maleate on casing/compost interface.

No additions to compost or casing

| | Flush 1 | Flush 2 | Cumulative | Flush 3 | Cumulative |
|---|---|---|---|---|---|
| Flush Weight Kg | 10485 | 11995 | 22480 | 4735 | 27215 |

Test Bed 14. 1100ml 5% Aqueous Calcium Maleate on days 3 and 5 after casing on casing top.

No addition to compost

| | Flush 1 | Flush 2 | Cumulative | Flush 3 | Cumulative |
|---|---|---|---|---|---|
| Flush Weight Kg | 12250 | 11850 | 24100 | 5000 | 29100 |

Test Bed 15. 1100ml 10% aqueous dispersion Calcium Maleate on days 3 and 5 after casing on casing top No addition to compost

| | Flush 1 | Flush 2 | Cumulative | Flush 3 | Cumulative |
|---|---|---|---|---|---|
| Flush Weight Kg | 9875 | 10700 | 20575 | 4770 | 25345 |

Test Bed 16. 1350grams commercial product. Formaldehyde treated Soya bean

*Comparative example* and poultry feathers mixed throughout the compost. No addition to casing

| | Flush 1 | Flush 2 | Cumulative | Flush 3 | Cumulative |
|---|---|---|---|---|---|
| Flush Weight Kg | 11010 | 12050 | 23060 | 6385 | 29445 |

Figure 9

METHOD TO IMPROVE MUSHROOM CULTIVATION

It is known that many substances may be utilised for growth by fungi. For commercial mushroom production compost rich in biomass protein and humic acid nitrogen complexes derived from bacterial and fungal composting of straws, manures etc is used as substrate for the mushroom mycelium grains and they are allowed to colonise the growing bed. After some 14 days at 25° C. the bed is covered (cased) with a layer consisting of 6 parts by volume of peat and 1 part by volume of sugarbeet fine chalk to a depth of 5-6 centimeters.

This nutritionally sterile layer is often mixed with particles of mycelium on a low nitrogen carrier in order to speed the link up and penetration into the casing layer of the compost mycelium.

When the casing layer has been penetrated by the compost mycelium the mushroom bed is cooled until primordia are formed and one week or so later the mushrooms are ready to harvest.

In order to get maximum yields of mushrooms per ton of compost, growers add extra nutrients to the compost. This may be in the form of formaldehyde denatured Soya products, feather meal or protein treated with antibacterial agents or carbohydrate, lipid and protein mixtures with calcium/amine salts of carboxylic acids.

These supplementary nutrients are normally added at a rate of from one to two percent on the weight of compost. It is essential to mix the supplementary nutrient very evenly throughout the compost bed. Any area with excess supplement will cause very dangerous heating effects and result in reduced yield and mycelium kill.

Areas with little or no supplement will of course not produce any yield increase.

The overall effect of uneven mixing of supplements is actually a reduced yield and high risk of disease within the growing bed. Even very well mixed supplemented growing beds show heat surges which have a high cost in terms of cooling technology in order to maintain optimum growing temperatures.

However in recent times the improved preparation of composts has raised the levels of naturally occurring protein nitrogen from an average of 2% in the 1980s to close to 3% at the present time.

Amounts of humic acids and partly soluble lignin humic acid nitrogen residues have also improved and the combined effect is for an improvement in natural nutrient levels in the compost which has meant that adding supplementary protein nutrients even at higher usage rates to the compost has had progressively less effect.

Up to 40% of the mass of a mushroom growing bed can be the casing layer. The function of this layer is to persuade the compost mycelium mass to form fruit bodies by virtue of the absence of nitrogenous nutrients in this top layer. As the mushrooms form in or on the casing layer the compost mycelium starts to transfer tissue nutrients from throughout the compost mass up to the casing layer to form the fruit bodies therein.

Early experiments to introduce particles of fully colonised compost into the casing in order to speed up the colonisation of the casing layer (cacing) frequently failed if nitrogen nutrient was introduced along with the mycelium particles on compost.

This resulted in cacing materials being developed using minimum nitrogen on vermiculite carrier for the mycelium.

It was clearly established that even very small amounts of nitrogen containing nutrient in the casing layer prevent the development of primordia—certainly below a threshold where any contribution to overall nutrition could be expected.

The mushroom industry subsequently regarded the casing layer as an area of nutritional sterility, which must be totally devoid of all nutrient value in order to function.

Salts of the carboxylic acids are also utilized by mushroom mycelium as an important nutrient source. Many of the carboxylic acid salts also have very active anti-mould properties.

There is a need for a novel method to substantially improve mushroom yields even at ultra low dose rates utilizing modern high nutrient composts that will not cause heating problems or disease risks for the mushroom grower

DESCRIPTION

Brief Description of the Drawings

FIG. 1 is a table describing exemplary cases.
FIG. 3 is a table describing exemplary cases, test beds 1 to 4.
FIG. 5 a table describing exemplary cases, test beds 5 to 8.
FIG. 7 a table describing exemplary cases, test beds 9 to 12.
FIG. 9 is a table describing exemplary cases, test beds 13 to 16.

Figure 2:
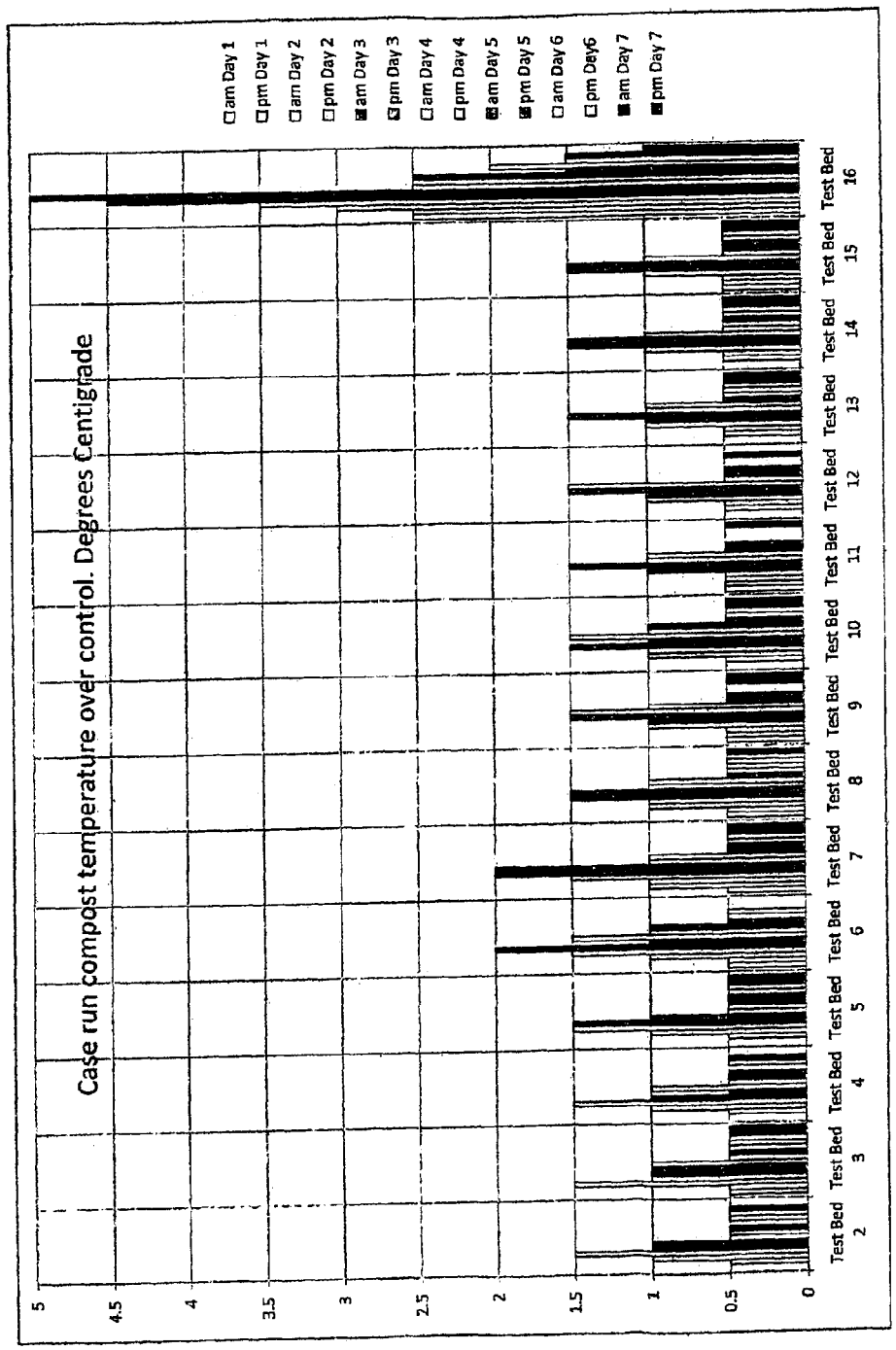
FIG. 2 is a chart describing exemplary cases.
Figure 4:
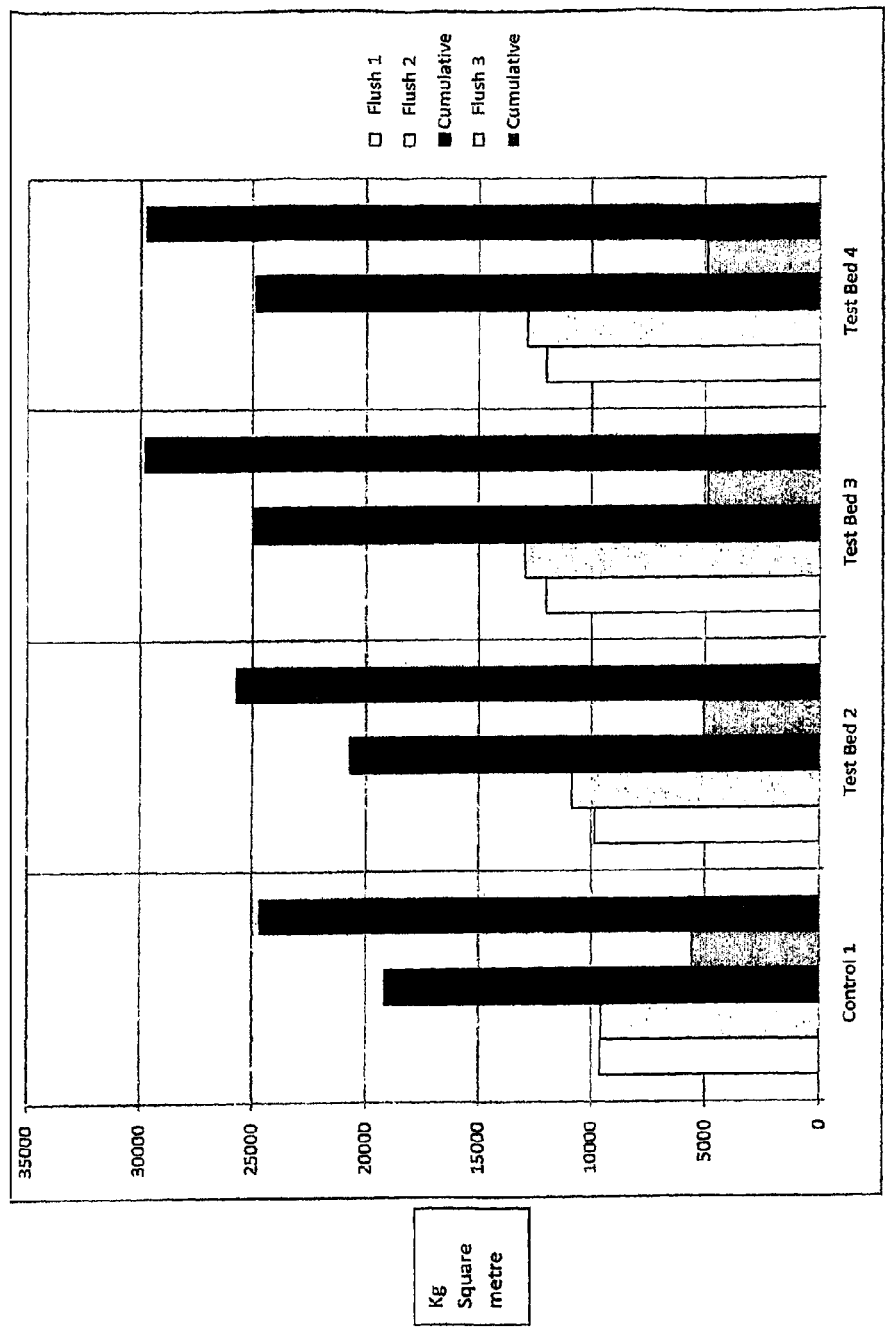
FIG. 4 is a chart describing exemplary cases, test beds 1 to 4.
Figure 6:
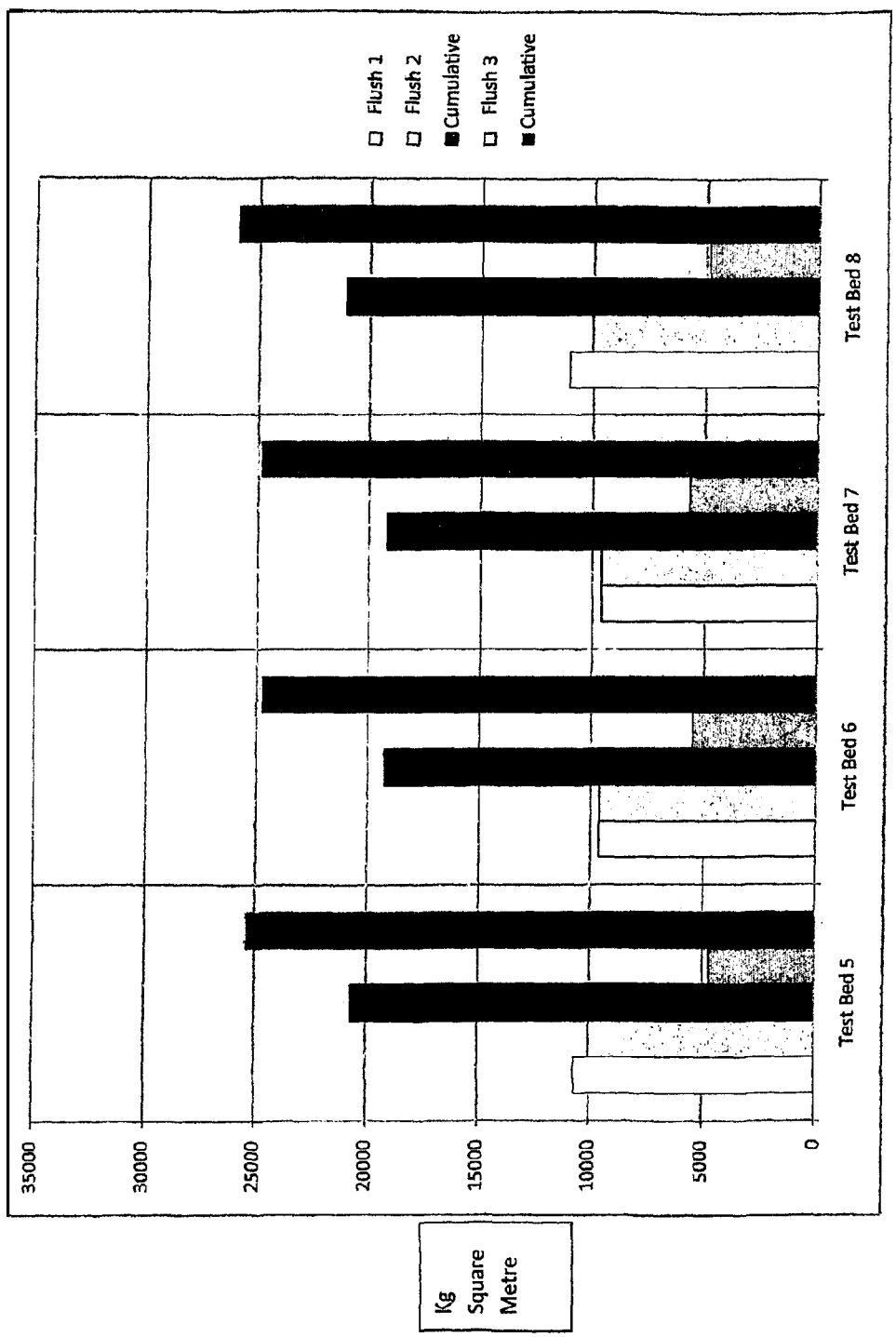
FIG. 6 is a chart describing exemplary cases, test beds 5 to 8.
Figure 8:
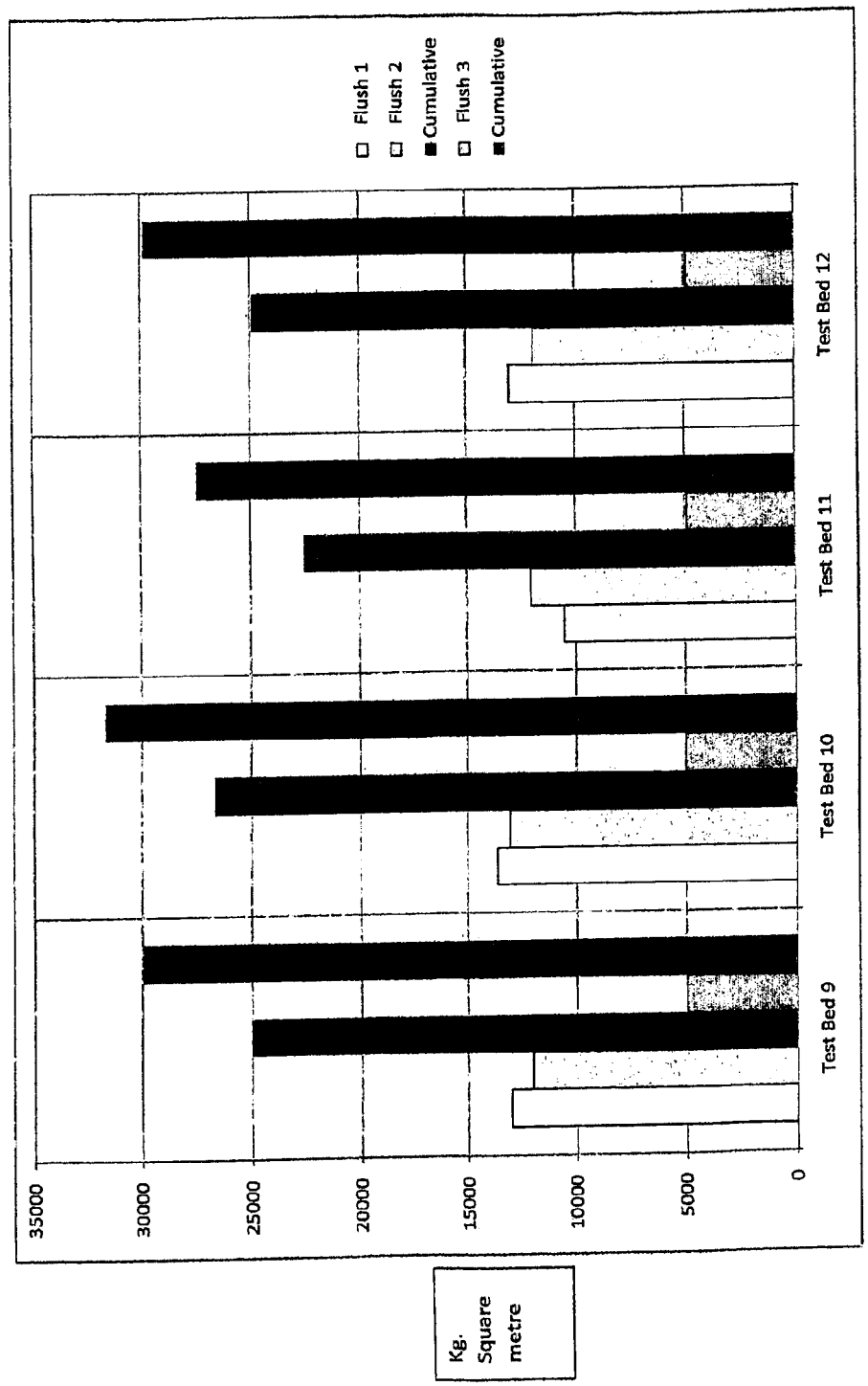
FIG. 8 is a chart describing exemplary cases, test beds 9 to 12.
Figure 10:
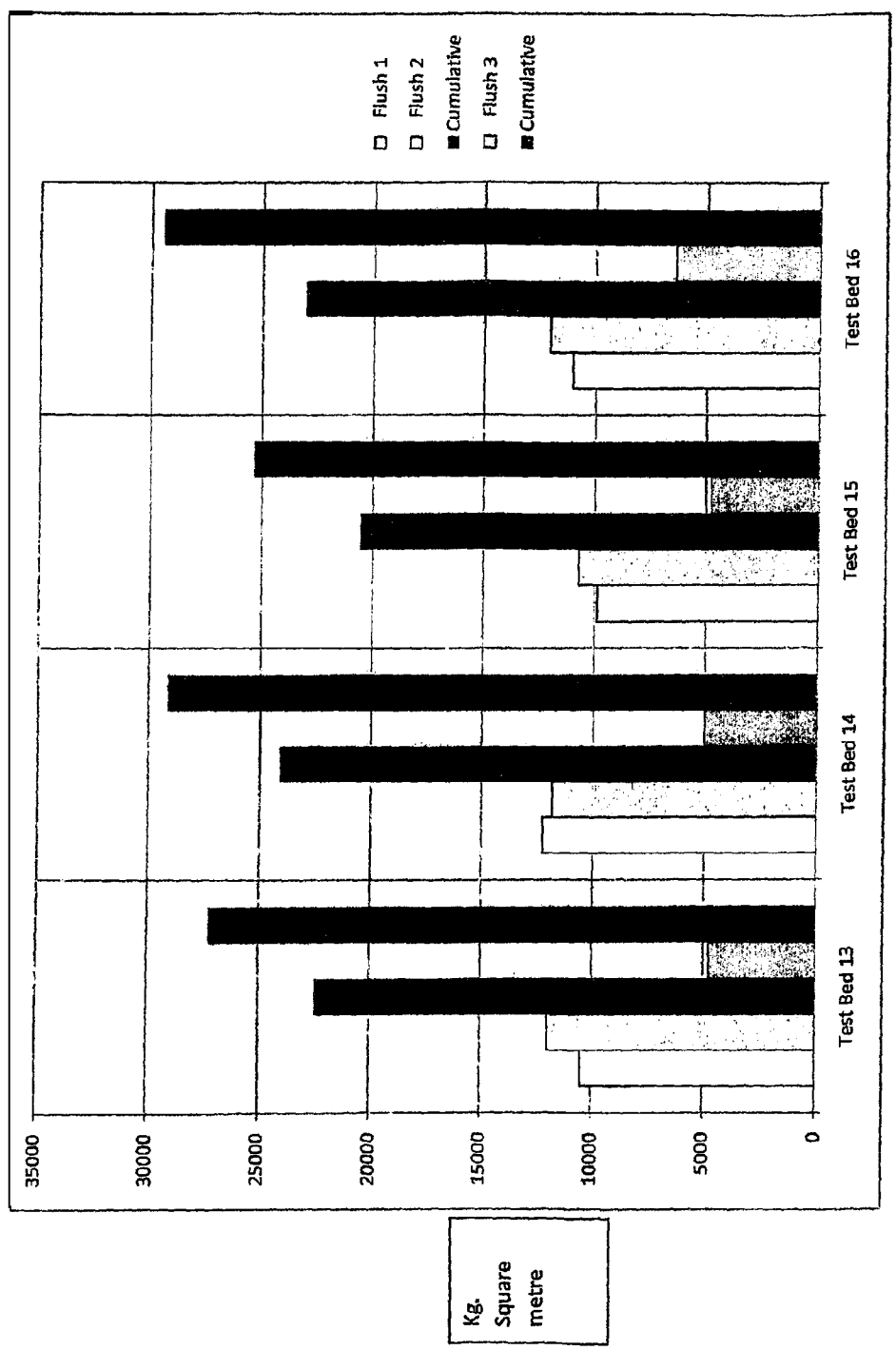
FIG. 10 is a chart describing exemplary cases, test beds 13 to 16.

A method and composition for improving the performance of a mushroom bed comprises adding a much reduced but effective amount of carboxylic acid salts or mixtures thereof to the casing layer or on the surface of the compost layer at the interface with the casing layer.

A method of improving the yield of mushroom growing beds comprising supplementing the casing layer or compost/casing interface with between 20 grams and 350 grams per square meter of mushroom bed surface area with an effective amount of a salt of aliphatic, aromatic, alicyclic, or heterocyclic carboxylic acid or mixtures thereof, the said salt being of potassium, magnesium or calcium or mixtures thereof wherein the nutrient salt or mixtures thereof must not be admixed with the compost layer more usually between 60 grams and 300 grams of carboxylic acid salts per square meter of mushroom bed surface area are used.

The effectiveness of this invention is a function of the surface of the growing bed and its micro supplementation and not in its admixture with the compost layer. The carboxylic salt nutrient is not mixed into the compost and so does not result in any significant heating effects.

Surprisingly it was found that a dose of one tenth of the normal supplement rate if mixed in with the casing layer or on the surface of the compost at the casing interface produces the same increase in yield as the normal amount of commercial supplement mixed throughout the compost.

It is suggested that the much enhanced yields obtained from a comparatively very small amount of nutrient is due to the placing of the supplement at or very near to the site of fruit body formation. That is, the mycelium in the compost does not have to transport the nutrients from deep within the compost layer to form the fruit body in the casing layer or compost interface.

The carboxylic salts may be derived from mono di or tri basic, aliphatic, hetrocyclic, aromatic or alicyclic, saturated or unsaturated, hydroxy or keto, straight or branch chained carboxylic acids or mixtures thereof.

Examples of such acids would be Propionic, Acetic, Lactic, Butyric, N-valeric, Pelargonic, Oleic, Linolenic, Linoleic, Salicylic, Gluconic, Hippuric, Malic, Maleic, Fumaric, Azelaic, Adipic, D & L Tartaric, Succinic, Furoic, Pyruvic, Glutaric, Citric or mixtures thereof.

In one embodiment the nutrient product may be prepared from ready made salts utilising cations such as potassium magnesium and preferably calcium and or mixtures thereof.

The product may also be formed in situ in the casing by adding acid salts or acids as granules, crystals, powders or solutions to the casing material with or without extra calcium cation depending on casing formulation.

The interface between compost and casing may also be utilised as a site for micro supplementation with salts of carboxylic acids as solutions, solutions/suspensions, suspensions, powders or granules.

In a further embodiment the carboxylic salts utilised as supplements on the compost/casing interface may include ammonia and organic amines as the cation. The ammonium and organic amine salts must not be used for incorporation into the casing layer as supplement.

The carboxylic salt containing nutrient may be incorporated into the casing layer in the form of powders or granules or in solutions or suspensions in water Modifying the solubility of the carboxylate salt powder or granules provides some control of availability of the nutrient over or up to four flushes.

Liquid carboxylic nutrient salts are best prepared by utilising the generally good solubility of the potassium salts of carboxylic acids but are best used as blends or double salts with calcium as the major cation.

An effective method of utilising the carboxylic nutrient salts is to water on a solution or suspension or combination of both on top of a casing layer two to three days after application of the casing when bridging has occurred between compost and casing.

The liquid nutrient may be applied as one application at a concentration of, for instance, ten percent or four or five daily applications at two percent to maintain casing moisture after day two after casing.

It is important to restrict the volume of nutrient solution in order to limit the penetration of the supplement into the surface of the compost. Excessive penetration much reduces the yield increase and allows heat surge to develop.

The carboxylic salt nutrient may be applied on the surface of the compost at the time the bed is spawned best results at this stage are by using the carboxylic salt nutrient as a granule or prill.

The carboxylic salt nutrient may be applied to the surface of fully-grown phase two compost prior to casing, which may be as granules, powder, solutions or suspensions.

Phase three compost may be surface supplemented with carboxylic salt nutrient prior to casing in any form prior to casing.

The carboxylic salt nutrient may be mixed with other nutrient substances in order to improve the performance of the nutrient mixture or to obtain specific nutrient effects.

In a further embodiment the carboxylic salt nutrient or mixtures thereof may be admixed with emulsifiers, clays, extenders, binders or absorbents in order to stabilise or modify the availability of the nutrient to the mushroom mycelium.

In a further aspect of our invention due to the well-documented anti-mould properties of the lower molecular weight carboxylate salts significant amounts of carbohydrates such as dextrins may be incorporated into the micro supplements.

Another aspect of our invention would include incorporation of lignin chemicals such as lignosulphonates derived from the paper industries in order to improve the nutritional balance of the supplement.

A further group of beneficial nutrients may be utilised in the supplement as described to be used on the compost surface but not as a casing supplement these are the soluble and semi-soluble amino acids and poly peptides.

A further embodiment of the invention is that significant amounts of unsaturated long chain carboxylic acid oils or salts thereof may be incorporated in the nutrient salts in order to improve mushroom quality and flavour.

The presence of lower molecular weight monocarboxylic acid salts in the critical areas of the casing and compost interface increases the selectivity of the growing bed against many fungal infections preferably no animal or vegetable products are added to the mushroom growing beds.

The term mushroom used in this context is meant to include any variety of *Agaricus* or any edible or medicinal fungus that may benefit from the technique of surface nutrient supplementation or casing enrichment eg. *Lepista Nuda, Calocybe Gambosa, Macrolepiota Procera, Calvatia Gigantean, Auricularia* spp., *Flammulina Velutipes, Boletus* spp., *Lentinula Edodes, Cantharellus* spp., *Morchella* spp., *Pholiota Nameko, Pleurotus* spp., *Stropharia rugosa-annluata, Tremeila Fuciformis, Volvariella Volvacea, Grifola Frondosa, Ganoderma* sp., *Polporus Umbellatus, Hericium Erinaceus, Coprinus Comatus, Agrocybe* sp.

Further examples of our invention are described by way of illustration only in the following non-limiting examples:

Examples

A casing supplement was prepared as follows 1 part by weight of 400 grams of Calcium Maleate powder 1 part by weight of 400 grams of cold water.

Were mixed into a smooth paste and spread onto a polytetra-fluoro-ethane coated plate and dried at 40 degrees centigrade for 12 hours. The dried thin sheet was broken up and sieve sized to 2.5 mm. Sixteen compost beds were prepared each with an area of 1 square meter containing 90 kgs of Phase Three compost prepared with Sylvan® A15 spawn. 40 kgs of Casing were prepared (6 parts by volume dark peat and 1 part by volume sugar beet chalk). This volume of casing will cover 1 square meter of growing bed to 4.5 cm deep.

The comparative results of the various possible techniques proposed by the top supplementation system are listed below. Also included is one plot for control and one plot for conventional high rate compost admixed supplement. All batches of casing were mixed with 100 grams of Sylvan A15® cacing just prior to application to the compost.

The examples show that a narrow band of concentration of nutrient is very effective within the casing layer or on the casing/compost interface. Excess of the supplement shows no commercial advantage as do test beds 6 and 7 where the supplement was mixed within the compost layer.

The invention claimed is:

1. A method of improving the yield of a mushroom growing bed comprising a compost layer, the method comprising:

supplementing a casing layer or compost/casing interface with a substance including a salt of aliphatic, aromatic, alicyclic, or heterocyclic carboxylic acids with a molecular weight of less than 300 or mixtures thereof, such that the salt acts as a mushroom nutrient, the salt being of potassium, magnesium or calcium or mixtures thereof; and not admixing the substance with the compost layer of the mushroom growing bed, wherein the supplementing step acts to supplement the casing layer or compost/casing interface with between 20 grams and 350 grams per square meter of mushroom bed surface area with the substance, to improve the yield of the mushroom growing bed.

2. A method as claimed in claim 1 wherein the substance is mixed with the casing layer with CACing (Compost At Casing) products.

3. A method as claimed as in claim 1 wherein the casing layer includes chalk and peat mixtures.

4. A method as claimed in claim 1 wherein the substance is presented at the surface of the compost at the interface with the casing layer.

5. A method as claimed in claim 4 wherein the carboxylic salts include ammonium or organic amine carboxylates in addition to the potassium, magnesium or calcium carboxylates.

6. A method as claimed in claim 1 wherein the acids are monocarboxylic, dicarboxylic or tricarboxylic or mixtures thereof.

7. A method as claimed in claim 1 where the carboxylic acids are saturated.

8. A method as claimed in claim 7 wherein the carboxylic acids have hydroxyl or keto substituents or mixtures thereof.

9. A method as claimed in claim 1 where the carboxylic salts are mixed with other nutrient substances to improve the performance of the product including dextrins, lignosulphonates, oils and long chain fatty acids and salts thereof.

10. A method as claimed in claim 9 wherein amino acids and or polypeptides are used in addition to dextrins, lignosulphonate, oils and long chain fatty acids and salts thereof only in the case of compost/casing interface presentation.

11. A method as claimed in claim 1 whereby the salts are utilised as a solution in water, a dispersion, a solution plus dispersion, a powder or a granule or prill.

12. A method as claimed in claim 1 whereby the salts are modified for ease of manufacture or application by mixture with emulsifiers, clays or extenders, binders or stabilizers or absorbents.

13. A method as claimed in claim 1 whereby the mushroom bed is supplemented by the carboxylic salts within the casing layer or on the compost interface with the casing layer at a rate of between 60 grams and 300 grams per square meter of the mushroom bed surface area.

14. A method as claimed in claim 1 whereby no heating surge occurs in the mushroom beds.

15. A method as claimed in claim 1 wherein the presence of the lower molecular weight monocarboxylic acid salts in the area of the casing and compost interface increases the selectivity of the growing bed against many fungal infections.

16. A method as claimed in claim 1 wherein the substance is mixed with the casing layer without CACing (Compost At Casing) products.

17. A method as claimed in claim 1 where the carboxylic acids are unsaturated.

* * * * *